United States Patent
Beal et al.

(10) Patent No.: US 8,608,702 B2
(45) Date of Patent: Dec. 17, 2013

(54) INTRODUCER INCLUDING SHAPED DISTAL REGION

(75) Inventors: James D. Beal, Spanish Fork, UT (US); Eric M. King, West Jordan, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 448 days.

(21) Appl. No.: 12/252,975

(22) Filed: Oct. 16, 2008

(65) Prior Publication Data

US 2009/0105652 A1    Apr. 23, 2009

Related U.S. Application Data

(60) Provisional application No. 60/981,418, filed on Oct. 19, 2007.

(51) Int. Cl.
    *A61M 5/178* (2006.01)
    *A61M 31/00* (2006.01)
    *A61M 37/00* (2006.01)

(52) U.S. Cl.
    USPC .............. 604/164.06; 604/93.01; 604/164.1

(58) Field of Classification Search
    USPC .............. 604/164.01, 164.02, 164.06, 506, 604/93.01, 164.1
    See application file for complete search history.

(56) References Cited

U.S. PATENT DOCUMENTS

| | | | |
|---|---|---|---|
| 675,157 A | 5/1901 | Howard | |
| 2,908,283 A | 10/1959 | Kiffer et al. | |
| 3,176,690 A | 4/1965 | H'Doubler | |
| D217,795 S | 6/1970 | Spaven | |
| 3,612,050 A | 10/1971 | Sheridan | |
| 3,805,794 A | 4/1974 | Schlesinger | |
| 3,853,127 A | 12/1974 | Spademan | |
| 4,000,739 A | 1/1977 | Stevens | |
| 4,068,659 A | 1/1978 | Moorehead | |
| 4,089,506 A | 5/1978 | Blake | |
| 4,143,853 A | 3/1979 | Abramson | |

(Continued)

FOREIGN PATENT DOCUMENTS

| EP | 0370721 A2 | 5/1990 |
|---|---|---|
| EP | 0442194 A2 | 8/1991 |

(Continued)

OTHER PUBLICATIONS

PCT/US2010/026409 filed Mar. 5, 2010 International Preliminary Report on Patentability dated Apr. 27, 2010.

(Continued)

*Primary Examiner* — Nicholas Lucchesi
*Assistant Examiner* — Rebecca E Eisenberg
(74) *Attorney, Agent, or Firm* — Rutan & Tucker LLP

(57) ABSTRACT

An introducer for providing intravascular access to a patient is disclosed, and includes a dilator and sheath that are configured to prevent peelback, or "fishmouthing," of the sheath during introducer advancement. In one embodiment, the introducer comprises a dilator including a distal tapered region, and a sheath including an inner bore that receives the dilator such that a portion of the tapered region of the dilator extends from the sheath distal end. A distal outer surface of the sheath includes a first curved portion defined by a first radius and extending proximally from the distal end of the sheath to a first end point, and a second curved portion defined by a second radius and extending proximally from the first end point to a second end point. Additionally, an interference fit is established between the dilator tapered region and the sheath distal end to further prevent sheath end deformation.

25 Claims, 8 Drawing Sheets

(56) References Cited

U.S. PATENT DOCUMENTS

| | | | |
|---|---|---|---|
| 4,198,973 A | 4/1980 | Millet | |
| 4,233,974 A | 11/1980 | Desecki et al. | |
| 4,296,747 A | 10/1981 | Ogle | |
| 4,306,562 A | 12/1981 | Osborne | |
| 4,411,654 A | 10/1983 | Boarini et al. | |
| 4,412,832 A | 11/1983 | Kling et al. | |
| 4,424,833 A | 1/1984 | Spector et al. | |
| 4,430,081 A | 2/1984 | Timmermans | |
| 4,431,426 A | 2/1984 | Groshong et al. | |
| 4,436,519 A | 3/1984 | O'Neill | |
| 4,445,893 A | 5/1984 | Bodicky | |
| 4,449,973 A | 5/1984 | Luther | |
| 4,453,928 A | 6/1984 | Steiger | |
| 4,468,224 A | 8/1984 | Enzmann et al. | |
| 4,473,067 A | 9/1984 | Schiff | |
| RE31,855 E | 3/1985 | Osborne | |
| 4,504,269 A | 3/1985 | Durand et al. | |
| 4,557,261 A | 12/1985 | Rugheimer et al. | |
| 4,571,241 A | 2/1986 | Christopher | |
| 4,581,012 A | 4/1986 | Brown et al. | |
| 4,581,025 A | 4/1986 | Timmermans | |
| 4,588,398 A * | 5/1986 | Daugherty et al. | 604/265 |
| 4,591,355 A | 5/1986 | Hilse | |
| 4,596,559 A | 6/1986 | Fleischhacker | |
| 4,610,665 A | 9/1986 | Matsumoto et al. | |
| 4,610,671 A | 9/1986 | Luther | |
| 4,619,643 A | 10/1986 | Bai | |
| 4,626,245 A | 12/1986 | Weinstein | |
| 4,634,432 A | 1/1987 | Kocak | |
| 4,650,472 A | 3/1987 | Bates | |
| 4,654,031 A | 3/1987 | Lentz | |
| 4,657,772 A | 4/1987 | Kocak | |
| 4,673,393 A | 6/1987 | Suzuki et al. | |
| 4,701,159 A | 10/1987 | Brown et al. | |
| 4,705,511 A | 11/1987 | Kocak | |
| 4,722,725 A | 2/1988 | Sawyer et al. | |
| 4,723,550 A | 2/1988 | Bales et al. | |
| 4,726,374 A | 2/1988 | Bales et al. | |
| 4,743,265 A | 5/1988 | Whitehouse et al. | |
| 4,747,833 A | 5/1988 | Kousai et al. | |
| 4,748,982 A | 6/1988 | Horzewski et al. | |
| 4,753,765 A | 6/1988 | Pande | |
| 4,772,266 A | 9/1988 | Groshong | |
| 4,784,644 A | 11/1988 | Sawyer et al. | |
| 4,795,426 A | 1/1989 | Jones | |
| 4,798,594 A | 1/1989 | Hillstead | |
| 4,809,679 A | 3/1989 | Shimonaka et al. | |
| 4,842,592 A | 6/1989 | Caggiani et al. | |
| 4,865,593 A | 9/1989 | Ogawa et al. | |
| 4,895,565 A | 1/1990 | Hillstead | |
| 4,909,798 A | 3/1990 | Fleischhacker et al. | |
| 4,921,479 A | 5/1990 | Grayzel | |
| 4,929,235 A | 5/1990 | Merry et al. | |
| 4,929,236 A | 5/1990 | Sampson | |
| 4,932,633 A | 6/1990 | Johnson et al. | |
| 4,935,010 A | 6/1990 | Cox et al. | |
| 4,936,826 A | 6/1990 | Amarasinghe | |
| 4,946,133 A | 8/1990 | Johnson et al. | |
| 4,952,359 A | 8/1990 | Wells | |
| 4,956,755 A | 9/1990 | Maglica et al. | |
| 4,960,412 A | 10/1990 | Fink | |
| 4,966,588 A | 10/1990 | Rayman et al. | |
| 4,973,312 A | 11/1990 | Andrew | |
| 4,983,168 A | 1/1991 | Moorehead | |
| 4,994,027 A | 2/1991 | Farrell | |
| 4,997,424 A | 3/1991 | Little | |
| 5,000,745 A | 3/1991 | Guest et al. | |
| 5,007,901 A | 4/1991 | Shields | |
| 5,009,391 A | 4/1991 | Steigerwald | |
| 5,011,478 A | 4/1991 | Cope | |
| 5,035,686 A | 7/1991 | Crittenden et al. | |
| 5,041,095 A | 8/1991 | Littrell | |
| 5,053,014 A | 10/1991 | Van Heugten | |
| 5,064,414 A | 11/1991 | Revane | |
| 5,066,285 A | 11/1991 | Hillstead | |
| 5,071,411 A | 12/1991 | Hillstead | |
| 5,078,688 A | 1/1992 | Lobodzinski et al. | |
| 5,085,645 A | 2/1992 | Purdy et al. | |
| 5,092,857 A | 3/1992 | Fleischhacker | |
| 5,098,392 A | 3/1992 | Fleischhacker et al. | |
| 5,098,393 A | 3/1992 | Amplatz et al. | |
| 5,102,395 A | 4/1992 | Cheer et al. | |
| 5,104,389 A | 4/1992 | Deem et al. | |
| 5,106,054 A | 4/1992 | Mollenauer et al. | |
| 5,112,301 A | 5/1992 | Fenton, Jr. et al. | |
| 5,114,408 A | 5/1992 | Fleischhaker et al. | |
| 5,117,836 A | 6/1992 | Millar | |
| 5,125,903 A | 6/1992 | McLaughlin et al. | |
| 5,125,904 A | 6/1992 | Lee | |
| 5,141,497 A | 8/1992 | Erskine | |
| 5,149,327 A | 9/1992 | Oshiyama et al. | |
| 5,154,701 A | 10/1992 | Cheer et al. | |
| 5,158,545 A | 10/1992 | Trudell et al. | |
| 5,160,323 A | 11/1992 | Andrew et al. | |
| 5,163,903 A | 11/1992 | Crittenden et al. | |
| 5,167,634 A | 12/1992 | Corrigan, Jr. et al. | |
| 5,167,637 A | 12/1992 | Okada et al. | |
| 5,169,393 A | 12/1992 | Moorehead et al. | |
| 5,171,222 A | 12/1992 | Euteneuer et al. | |
| 5,176,652 A | 1/1993 | Littrell | |
| 5,180,372 A | 1/1993 | Vegoe et al. | |
| 5,190,529 A | 3/1993 | McCrory et al. | |
| 5,191,898 A | 3/1993 | Millar | |
| 5,197,976 A | 3/1993 | Herweck et al. | |
| 5,201,722 A | 4/1993 | Moorehead et al. | |
| 5,205,834 A | 4/1993 | Moorehead et al. | |
| 5,207,649 A | 5/1993 | Aruny | |
| 5,211,633 A | 5/1993 | Stouder, Jr. | |
| 5,215,538 A | 6/1993 | Larkin | |
| 5,221,263 A | 6/1993 | Sinko et al. | |
| 5,224,930 A | 7/1993 | Spaeth et al. | |
| 5,234,407 A | 8/1993 | Teirstein et al. | |
| 5,234,410 A | 8/1993 | Graham et al. | |
| 5,234,438 A | 8/1993 | Semrad | |
| 5,242,413 A | 9/1993 | Heiliger | |
| 5,242,430 A | 9/1993 | Arenas et al. | |
| 5,242,431 A | 9/1993 | Kristiansen | |
| 5,250,033 A | 10/1993 | Evans et al. | |
| 5,255,691 A | 10/1993 | Otten | |
| 5,269,771 A | 12/1993 | Thomas et al. | |
| 5,273,540 A | 12/1993 | Luther et al. | |
| 5,273,546 A | 12/1993 | McLaughlin et al. | |
| 5,275,583 A | 1/1994 | Crainich | |
| 5,279,597 A | 1/1994 | Dassa et al. | |
| 5,290,294 A | 3/1994 | Cox et al. | |
| 5,292,311 A | 3/1994 | Cope | |
| 5,304,142 A | 4/1994 | Liebl et al. | |
| 5,304,156 A | 4/1994 | Sylvanowicz et al. | |
| 5,306,240 A | 4/1994 | Berry | |
| 5,312,355 A | 5/1994 | Lee | |
| 5,312,357 A | 5/1994 | Buijs et al. | |
| 5,318,542 A | 6/1994 | Hirsch et al. | |
| 5,320,602 A | 6/1994 | Karpiel | |
| 5,324,271 A | 6/1994 | Abiuso et al. | |
| 5,334,157 A | 8/1994 | Klein et al. | |
| 5,334,187 A | 8/1994 | Fischell et al. | |
| 5,336,192 A | 8/1994 | Palestrant | |
| 5,348,537 A | 9/1994 | Wiesner et al. | |
| 5,350,362 A | 9/1994 | Stouder, Jr. | |
| 5,350,363 A | 9/1994 | Goode et al. | |
| 5,364,393 A | 11/1994 | Auth et al. | |
| 5,368,574 A | 11/1994 | Antonacci et al. | |
| 5,382,241 A | 1/1995 | Choudhury et al. | |
| 5,389,081 A | 2/1995 | Castro | |
| 5,389,090 A | 2/1995 | Fischell et al. | |
| 5,391,152 A | 2/1995 | Patterson | |
| 5,395,352 A | 3/1995 | Penny | |
| 5,397,310 A | 3/1995 | Chu et al. | |
| 5,397,311 A | 3/1995 | Walker et al. | |
| 5,405,320 A | 4/1995 | Twardowski et al. | |
| 5,405,323 A | 4/1995 | Rogers et al. | |
| 5,405,329 A | 4/1995 | Durand et al. | |
| 5,409,463 A | 4/1995 | Thomas et al. | |
| 5,409,464 A | 4/1995 | Villalobos | |

(56) References Cited

U.S. PATENT DOCUMENTS

| | | |
|---|---|---|
| 5,409,469 A | 4/1995 | Schaerf |
| 5,413,561 A | 5/1995 | Fischell et al. |
| 5,419,340 A | 5/1995 | Stevens |
| 5,423,762 A | 6/1995 | Hillstead |
| 5,429,616 A | 7/1995 | Schaffer |
| 5,437,645 A | 8/1995 | Urban et al. |
| 5,441,504 A | 8/1995 | Pohndorf et al. |
| 5,453,095 A | 9/1995 | Davila et al. |
| 5,460,616 A | 10/1995 | Weinstein et al. |
| 5,466,230 A | 11/1995 | Davila |
| 5,472,418 A | 12/1995 | Palestrant |
| 5,472,435 A | 12/1995 | Sutton |
| 5,474,099 A | 12/1995 | Boehmer et al. |
| 5,474,544 A | 12/1995 | Lynn |
| 5,484,401 A | 1/1996 | Rodriguez et al. |
| 5,488,960 A | 2/1996 | Toner |
| 5,489,273 A | 2/1996 | Whitney et al. |
| 5,496,346 A | 3/1996 | Horzewski et al. |
| 5,499,975 A | 3/1996 | Cope et al. |
| 5,501,676 A | 3/1996 | Niedospial et al. |
| 5,509,897 A | 4/1996 | Twardowski et al. |
| 5,520,655 A | 5/1996 | Davila et al. |
| 5,536,255 A | 7/1996 | Moss |
| 5,538,505 A | 7/1996 | Weinstein et al. |
| 5,549,651 A | 8/1996 | Lynn |
| 5,556,387 A | 9/1996 | Mollenauer et al. |
| 5,558,652 A | 9/1996 | Henke |
| 5,599,305 A | 2/1997 | Hermann et al. |
| 5,603,702 A | 2/1997 | Smith et al. |
| 5,613,953 A | 3/1997 | Pohndorf |
| 5,613,956 A | 3/1997 | Patterson et al. |
| 5,647,857 A | 7/1997 | Anderson et al. |
| 5,653,697 A | 8/1997 | Quiachon et al. |
| 5,653,698 A | 8/1997 | Niedospial et al. |
| 5,662,606 A | 9/1997 | Cimino et al. |
| 5,672,158 A | 9/1997 | Okada et al. |
| 5,685,856 A | 11/1997 | Lehrer |
| 5,685,858 A | 11/1997 | Kawand |
| 5,702,370 A | 12/1997 | Sylvanowicz et al. |
| 5,713,867 A | 2/1998 | Morris |
| 5,727,770 A | 3/1998 | Dennis |
| 5,735,819 A | 4/1998 | Elliott |
| 5,741,233 A | 4/1998 | Riddle et al. |
| 5,741,234 A | 4/1998 | Aboul-Hosn |
| 5,752,937 A | 5/1998 | Otten et al. |
| 5,755,693 A | 5/1998 | Walker et al. |
| 5,755,702 A | 5/1998 | Hillstead et al. |
| 5,766,203 A | 6/1998 | Imran et al. |
| 5,772,678 A | 6/1998 | Thomason et al. |
| 5,782,807 A | 7/1998 | Falvai et al. |
| 5,782,812 A | 7/1998 | Hart et al. |
| 5,782,817 A | 7/1998 | Franzel et al. |
| 5,800,414 A | 9/1998 | Cazal et al. |
| 5,807,350 A | 9/1998 | Diaz |
| 5,817,069 A | 10/1998 | Arnett |
| 5,843,031 A | 12/1998 | Hermann et al. |
| 5,853,393 A | 12/1998 | Bogert |
| 5,858,007 A | 1/1999 | Fagan et al. |
| 5,879,333 A | 3/1999 | Smith et al. |
| 5,885,217 A | 3/1999 | Gisselberg et al. |
| 5,895,376 A | 4/1999 | Schwartz et al. |
| 5,911,710 A | 6/1999 | Barry et al. |
| 5,916,194 A | 6/1999 | Jacobsen et al. |
| 5,919,160 A | 7/1999 | Sanfilippo, II |
| 5,921,968 A | 7/1999 | Lampropoulos et al. |
| 5,935,112 A | 8/1999 | Stevens et al. |
| 5,935,122 A | 8/1999 | Fourkas et al. |
| 5,944,695 A | 8/1999 | Johnson et al. |
| 5,951,518 A | 9/1999 | Licata et al. |
| 5,957,912 A | 9/1999 | Heitzmann |
| 5,967,490 A | 10/1999 | Pike |
| 5,971,958 A | 10/1999 | Zhang |
| 5,997,562 A | 12/1999 | Zadno-Azizi et al. |
| 6,017,352 A | 1/2000 | Nash et al. |
| 6,024,729 A | 2/2000 | Dehdashtian et al. |
| 6,027,480 A | 2/2000 | Davis et al. |
| 6,033,375 A | 3/2000 | Brumbach |
| 6,033,388 A | 3/2000 | Nordstrom et al. |
| 6,053,904 A | 4/2000 | Scribner et al. |
| 6,074,377 A | 6/2000 | Sanfilippo, II |
| 6,080,141 A | 6/2000 | Castro et al. |
| 6,083,207 A | 7/2000 | Heck |
| 6,086,570 A | 7/2000 | Aboul-Hosn et al. |
| 6,088,889 A | 7/2000 | Luther et al. |
| 6,106,540 A | 8/2000 | White et al. |
| 6,120,476 A | 9/2000 | Fung et al. |
| 6,120,480 A | 9/2000 | Zhang et al. |
| 6,120,494 A * | 9/2000 | Jonkman ................. 604/506 |
| 6,142,981 A | 11/2000 | Heck et al. |
| 6,156,054 A | 12/2000 | Zadno-Azizi et al. |
| 6,159,198 A | 12/2000 | Gardeski et al. |
| 6,162,196 A | 12/2000 | Hart et al. |
| 6,171,281 B1 | 1/2001 | Zhang |
| 6,210,366 B1 | 4/2001 | Sanfilippo, II |
| 6,213,988 B1 | 4/2001 | McIvor et al. |
| 6,221,057 B1 | 4/2001 | Schwartz et al. |
| 6,228,062 B1 | 5/2001 | Howell et al. |
| 6,251,119 B1 | 6/2001 | Addis |
| 6,258,058 B1 | 7/2001 | Sanfilippo, II |
| 6,273,871 B1 | 8/2001 | Davis et al. |
| 6,276,661 B1 | 8/2001 | Laird |
| 6,277,108 B1 | 8/2001 | McBroom et al. |
| 6,287,280 B1 | 9/2001 | Lampropoulos et al. |
| D450,839 S | 11/2001 | Junker |
| 6,322,541 B2 | 11/2001 | West et al. |
| 6,331,176 B1 | 12/2001 | Becker et al. |
| 6,338,725 B1 | 1/2002 | Hermann et al. |
| 6,352,520 B1 | 3/2002 | Miyazaki et al. |
| 6,358,460 B1 | 3/2002 | Hunt, Jr. et al. |
| 6,361,559 B1 | 3/2002 | Houser et al. |
| 6,375,157 B1 | 4/2002 | Van de Lande |
| 6,402,723 B1 | 6/2002 | Lampropoulos et al. |
| 6,413,250 B1 | 7/2002 | Smith et al. |
| 6,416,499 B2 | 7/2002 | Paul, Jr. |
| 6,454,744 B1 | 9/2002 | Spohn et al. |
| 6,458,103 B1 | 10/2002 | Albert et al. |
| 6,494,860 B2 | 12/2002 | Rocamora et al. |
| 6,497,681 B1 | 12/2002 | Brenner |
| 6,508,790 B1 | 1/2003 | Lawrence |
| 6,520,939 B2 | 2/2003 | Lafontaine |
| 6,544,247 B1 | 4/2003 | Gardeski et al. |
| 6,551,283 B1 | 4/2003 | Guo et al. |
| 6,575,960 B2 | 6/2003 | Becker et al. |
| 6,589,214 B2 | 7/2003 | McGuckin, Jr. et al. |
| 6,589,262 B1 | 7/2003 | Honebrink et al. |
| 6,592,544 B1 | 7/2003 | Mooney et al. |
| 6,592,553 B2 | 7/2003 | Zhang et al. |
| 6,595,959 B2 | 7/2003 | Stratienko |
| 6,599,302 B2 | 7/2003 | Houser et al. |
| 6,623,460 B1 | 9/2003 | Heck |
| 6,632,200 B2 | 10/2003 | Guo et al. |
| 6,632,234 B2 | 10/2003 | Kieturakis et al. |
| 6,638,242 B2 | 10/2003 | Wilson et al. |
| 6,641,564 B1 | 11/2003 | Kraus |
| 6,645,178 B1 | 11/2003 | Junker et al. |
| 6,652,492 B1 | 11/2003 | Bell et al. |
| 6,655,660 B2 | 12/2003 | Wales |
| 6,663,595 B2 | 12/2003 | Spohn et al. |
| 6,666,853 B2 | 12/2003 | Chu et al. |
| 6,682,498 B2 | 1/2004 | Ross |
| 6,682,519 B1 | 1/2004 | Schon |
| 6,692,464 B2 | 2/2004 | Graf |
| 6,695,810 B2 | 2/2004 | Peacock, III et al. |
| 6,695,832 B2 | 2/2004 | Schon et al. |
| 6,712,789 B1 | 3/2004 | Lange et al. |
| 6,712,791 B2 | 3/2004 | Lui et al. |
| 6,719,749 B1 | 4/2004 | Schweikert et al. |
| 6,740,101 B2 | 5/2004 | Houser et al. |
| 6,776,774 B2 | 8/2004 | Tansey, Jr. et al. |
| 6,796,991 B2 | 9/2004 | Nardeo |
| 6,808,502 B2 | 10/2004 | Nguyen |
| 6,808,509 B1 | 10/2004 | Davey |
| 6,808,520 B1 | 10/2004 | Fourkas et al. |
| 6,814,718 B2 | 11/2004 | McGuckin, Jr. et al. |

(56) References Cited

U.S. PATENT DOCUMENTS

| | | | |
|---|---|---|---|
| 6,827,709 B2 | 12/2004 | Fujii | |
| 6,827,710 B1 | 12/2004 | Mooney et al. | |
| 6,872,198 B1 | 3/2005 | Wilson et al. | |
| 6,881,211 B2 | 4/2005 | Schweikert et al. | |
| 6,887,220 B2 | 5/2005 | Hogendijk | |
| 6,887,417 B1 | 5/2005 | Gawreluk et al. | |
| 6,913,594 B2 | 7/2005 | Coleman et al. | |
| 6,916,313 B2 | 7/2005 | Cunningham | |
| 6,966,886 B2 | 11/2005 | Appling | |
| 7,001,396 B2 | 2/2006 | Glazier et al. | |
| 7,017,886 B1 | 3/2006 | Ngene-Igwe | |
| 7,100,690 B2 | 9/2006 | Mullen et al. | |
| 7,100,890 B2 | 9/2006 | Cote, Sr. et al. | |
| 7,101,353 B2 | 9/2006 | Lui et al. | |
| 7,166,088 B2 | 1/2007 | Heuser | |
| 7,192,433 B2 | 3/2007 | Osypka et al. | |
| 7,294,296 B2 | 11/2007 | Davey | |
| 7,524,305 B2 | 4/2009 | Moyer | |
| 7,637,893 B2 | 12/2009 | Christensen et al. | |
| 8,105,315 B2 | 1/2012 | Johnson et al. | |
| 2001/0001813 A1 | 5/2001 | West et al. | |
| 2001/0041872 A1 | 11/2001 | Paul | |
| 2001/0041873 A1 | 11/2001 | Dopper et al. | |
| 2001/0041875 A1* | 11/2001 | Higuchi et al. | 604/272 |
| 2001/0049499 A1* | 12/2001 | Lui et al. | 604/164.05 |
| 2002/0010425 A1 | 1/2002 | Guo et al. | |
| 2002/0038106 A1 | 3/2002 | Fujii | |
| 2002/0042789 A1 | 4/2002 | Michalewicz et al. | |
| 2002/0055715 A1 | 5/2002 | Young et al. | |
| 2002/0068898 A1 | 6/2002 | McGuckin et al. | |
| 2002/0068899 A1 | 6/2002 | McGuckin et al. | |
| 2002/0072789 A1 | 6/2002 | Hackett et al. | |
| 2002/0107482 A1 | 8/2002 | Rocamora et al. | |
| 2003/0014015 A1 | 1/2003 | Tansey et al. | |
| 2003/0050604 A1 | 3/2003 | Lui et al. | |
| 2003/0163139 A1 | 8/2003 | Graf | |
| 2003/0216771 A1 | 11/2003 | Osypka et al. | |
| 2004/0006330 A1 | 1/2004 | Fangrow | |
| 2004/0030319 A1 | 2/2004 | Korkor et al. | |
| 2004/0049499 A1 | 3/2004 | Nomoto et al. | |
| 2004/0059296 A1 | 3/2004 | Godfrey | |
| 2004/0065333 A1 | 4/2004 | Wilson et al. | |
| 2004/0082913 A1 | 4/2004 | Spohn et al. | |
| 2004/0092863 A1 | 5/2004 | Raulerson et al. | |
| 2004/0092879 A1 | 5/2004 | Kraus et al. | |
| 2004/0097863 A1 | 5/2004 | Appling | |
| 2004/0097903 A1 | 5/2004 | Raulerson | |
| 2004/0103229 A1 | 5/2004 | Callum | |
| 2004/0122418 A1 | 6/2004 | Voorhees | |
| 2004/0158208 A1 | 8/2004 | Hiejima | |
| 2004/0167478 A1 | 8/2004 | Mooney et al. | |
| 2004/0171997 A1 | 9/2004 | Wilson et al. | |
| 2004/0172003 A1 | 9/2004 | Wilson et al. | |
| 2004/0176739 A1 | 9/2004 | Stephens et al. | |
| 2004/0176744 A1 | 9/2004 | Lange et al. | |
| 2004/0176781 A1 | 9/2004 | Lindstrom et al. | |
| 2004/0186444 A1 | 9/2004 | Daly et al. | |
| 2004/0193112 A1 | 9/2004 | Glazier et al. | |
| 2004/0193119 A1 | 9/2004 | Canaud et al. | |
| 2004/0243095 A1 | 12/2004 | Nimkar et al. | |
| 2004/0254534 A1 | 12/2004 | Bjorkman et al. | |
| 2004/0254541 A1 | 12/2004 | Wong et al. | |
| 2004/0260243 A1 | 12/2004 | Rickerd | |
| 2004/0267202 A1 | 12/2004 | Potter | |
| 2005/0010238 A1 | 1/2005 | Potter et al. | |
| 2005/0027257 A1 | 2/2005 | Davey | |
| 2005/0049555 A1 | 3/2005 | Moorehead et al. | |
| 2005/0049628 A1 | 3/2005 | Schweikert et al. | |
| 2005/0090779 A1 | 4/2005 | Osypka | |
| 2005/0113805 A1 | 5/2005 | Devellian et al. | |
| 2005/0245874 A1 | 11/2005 | Carrez et al. | |
| 2005/0257838 A1 | 11/2005 | Enerson | |
| 2005/0267487 A1 | 12/2005 | Christensen et al. | |
| 2006/0030817 A1 | 2/2006 | Kraus et al. | |
| 2006/0052749 A1 | 3/2006 | Moyer | |
| 2006/0149293 A1 | 7/2006 | King et al. | |
| 2007/0123825 A1 | 5/2007 | King et al. | |
| 2007/0135794 A1 | 6/2007 | Raulerson et al. | |
| 2008/0051717 A1 | 2/2008 | Voss et al. | |
| 2008/0097386 A1 | 4/2008 | Osypka | |
| 2008/0300538 A1 | 12/2008 | Schweikert et al. | |
| 2009/0131873 A1 | 5/2009 | Spear et al. | |
| 2009/0143739 A1 | 6/2009 | Nardeo et al. | |
| 2009/0177163 A1 | 7/2009 | King et al. | |
| 2009/0218728 A1 | 9/2009 | Moyer | |
| 2009/0234290 A1 | 9/2009 | Fisher et al. | |
| 2009/0299291 A1 | 12/2009 | Baid | |
| 2010/0101069 A1 | 4/2010 | Christensen et al. | |
| 2012/0143138 A1 | 6/2012 | King et al. | |

FOREIGN PATENT DOCUMENTS

| | | |
|---|---|---|
| EP | 1240916 A1 | 9/2002 |
| IN | 2762/DELNP/2010 | 10/2011 |
| JP | 2007511089 T | 4/2007 |
| WO | 9813083 A1 | 4/1998 |
| WO | 0149363 A1 | 7/2001 |
| WO | 2004103229 A1 | 12/2004 |
| WO | 2005107843 A1 | 11/2005 |
| WO | 2007050788 A2 | 5/2007 |
| WO | 2007052278 A2 | 5/2007 |
| WO | 2009097274 A2 | 8/2009 |
| WO | 2009114456 A1 | 9/2009 |
| WO | 2010102240 A1 | 9/2010 |
| WO | 2012083245 A1 | 6/2012 |

OTHER PUBLICATIONS

U.S. Appl. No. 12/648,533, filed Dec. 29, 2009 Final Office Action dated Jan. 19, 2011.
Hazard Report—ECRI Problem Rerporting System, Health Devices, May-Jun. 1996; vol. 25, No. 5-6, pp. 214-215.
PCT/US2005/015253 filed May 2, 2005 Preliminary Report on Patentability dated Nov. 1, 2006.
PCT/US2005/015253 filed May 2, 2005 Search Report dated Aug. 4, 2005.
PCT/US2005/015253 filed May 2, 2005 Written Opinion dated Aug. 4, 2005.
PCT/US2008/080227 filed Oct. 16, 2008 Preliminary Report on Patentability dated Apr. 20, 2010.
PCT/US2008/080227 filed Oct. 16, 2008 Search Report dated Dec. 23, 2008.
PCT/US2008/080227 filed Oct. 16, 2008 Written Opinion dated Dec. 23, 2008.
PCT/US2010/026409 filed Mar. 5, 2010 Search Report dated Apr. 27, 2010.
PCT/US2010/026409 filed Mar. 5, 2010 Written Opinion dated Apr. 27, 2010.
U.S. Appl. No. 11/288,959, filed Nov. 29, 2005 Final Office Action dated Jun. 22, 2009.
U.S. Appl. No. 11/288,959, filed Nov. 29, 2005 Non-Final Office Action dated Oct. 20, 2008.
U.S. Appl. No. 12/648,533, filed Dec. 29, 2009 Non-Final Office Action dated Sep. 13, 2010.
CN 200880121184.X filed Oct. 16, 2008 Office Action dated Feb. 16, 2012.
PCT/US2011/065632 filed Dec. 16, 2011 International Search Report dated Apr. 4, 2012.
PCT/US2011/065632 filed Dec. 16, 2011 Written Opinion dated Apr. 4, 2012.
U.S. Appl. No. 11/531,339, filed Sep. 13, 2006 Non-Final Office Action dated Dec. 27, 2011.
U.S. Appl. No. 12/399,749, filed Mar. 6, 2009 Non-Final Office Action dated Mar. 28, 2012.
U.S. Appl. No. 12/648,533, filed Dec. 29, 2009 Examiner's Answer dated Dec. 22, 2011.
U.S. Appl. No. 12/648,533, filed Dec. 29, 2009 Notice of Panel Decision dated Jun. 16, 2011.
US 5,520,663, 05/1996, Patterson et al. (withdrawn)

* cited by examiner

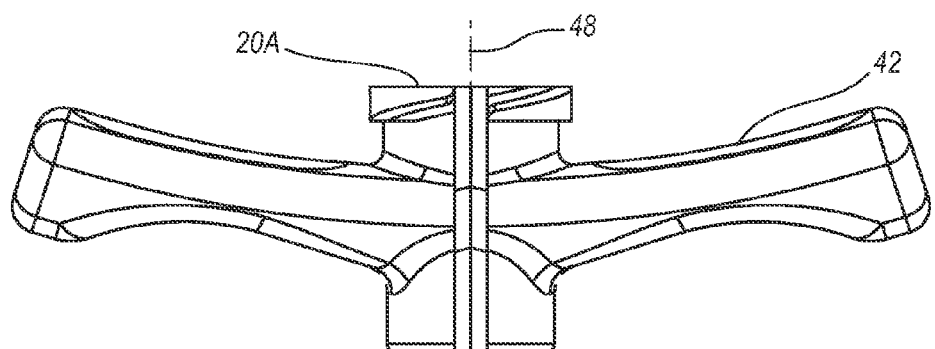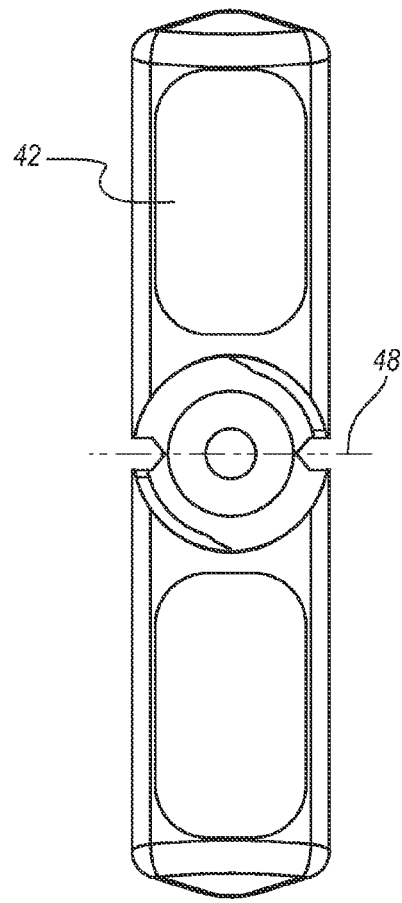
FIG. 2A
FIG. 2B

INTRODUCER INCLUDING SHAPED DISTAL REGION

CROSS-REFERENCE TO RELATED APPLICATIONS

This application claims the benefit of U.S. Provisional Patent Application No. 60/981,418, filed Oct. 19, 2007, and entitled "Introducer Sheath Having Shaped Distal End," which is incorporated herein by reference in its entirety.

BRIEF SUMMARY

Briefly summarized, embodiments of the present invention are directed to an introducer for providing intravascular access to a patient. Advantageously, the introducer includes a dilator and sheath that are configured to prevent peelback, or "fishmouthing," of the sheath during introducer advancement into the vasculature, often a problem with known introducer designs.

In one embodiment, the introducer comprises a dilator including a distal tapered region, and a sheath including an inner bore that receives the dilator such that a portion of the tapered region of the dilator extends from the sheath distal end. A distal outer surface of the sheath includes a first curved portion defined in cross section by a first radius and extending proximally from the distal end of the sheath to a first end point. The distal outer surface of the sheath further includes a second curved portion defined in cross section by a second radius and extending proximally from the first end point to a second end point. The first and second curved portions define a smoothly shaped distal region on the outer surface of the sheath, thus enabling the sheath to advance smoothly through an incision in a vein or other vessel into which the introducer is to be inserted and reducing the likelihood of sheath distal end deformation.

Additionally, an interference fit is established in one embodiment between the tapered region of the dilator and the sheath distal end by sizing the tapered region to extend proximally through the sheath distal end and into the sheath's inner bore a predetermined distance. This provides a relatively gap-free fit between the distal end of the sheath and the tapered dilator, further serving to prevent sheath end deformation.

These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof that are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 2A is a partial cross sectional side view of a sheath assembly of the introducer shown in FIG. 1A;

FIG. 2B is an end view of the sheath assembly of FIG. 2A;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the invention, and are not limiting of the present invention nor are they necessarily drawn to scale.

FIGS. 1A-9B depict various features of embodiments of the present invention, which are generally directed to an introducer for use in facilitating intravascular access to the body of a patient. Such access is desired in connection with the intravascular insertion a medical device, such as a peripherally inserted central catheter ("PICC") or other catheter, for instance.

Advantageously, the introducer includes a dilator and sheath that are configured in such a way as to improve insertion of the introducer tip into a vein or other portion of a patient's vasculature. In particular, the interface region of the dilator and sheath is configured so as to prevent peelback, or "fishmouthing," of the sheath distal end during advancement of the introducer, a problem often encountered with known sheath designs, especially those composed of polytetrafluoroethylene ("PTFE").

Figure 1A:
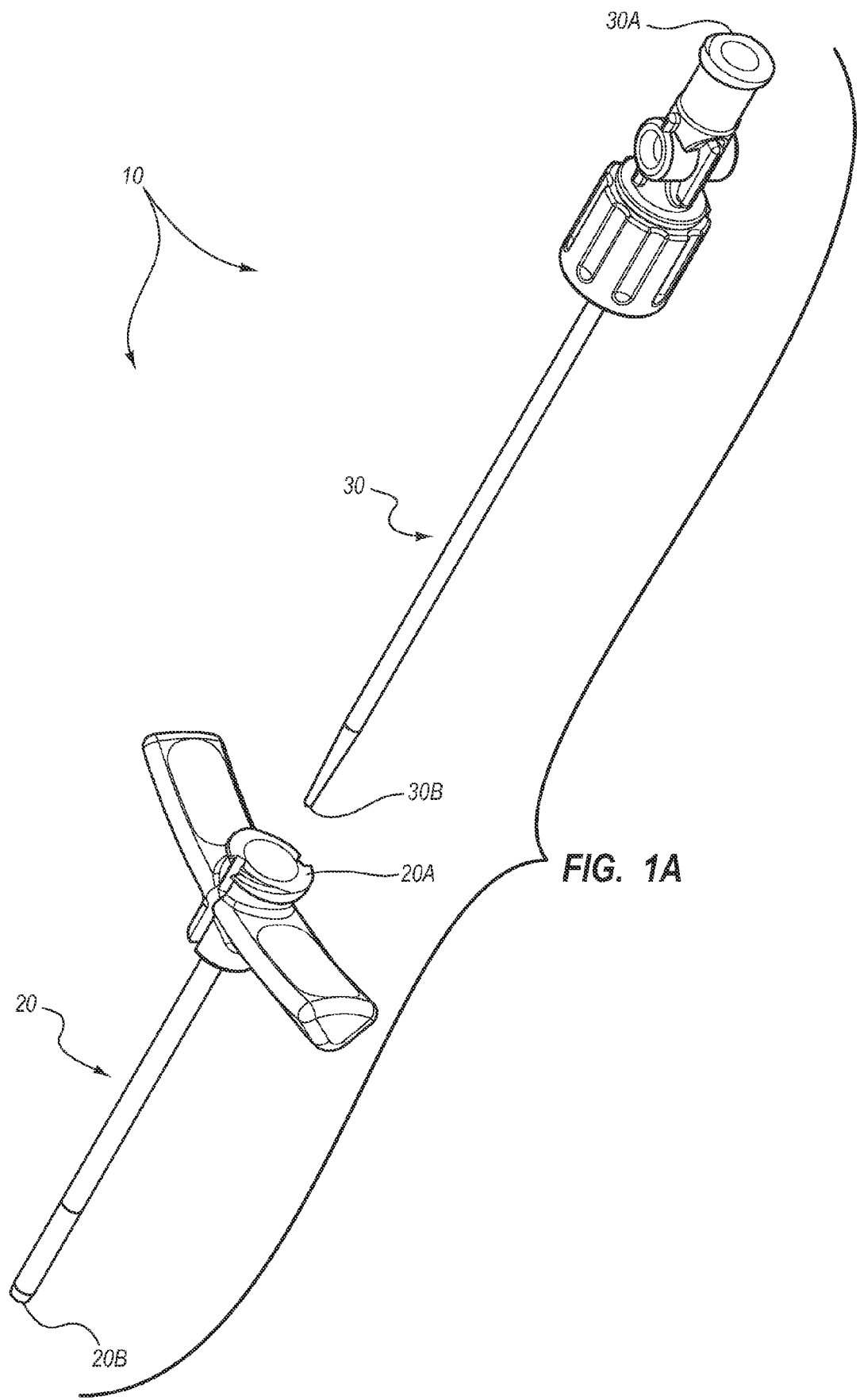
FIG. 1A is a partially exploded, perspective view of an introducer including a sheath defining a shaped distal region in accordance with an example embodiment of the present invention.
Figure 1B:
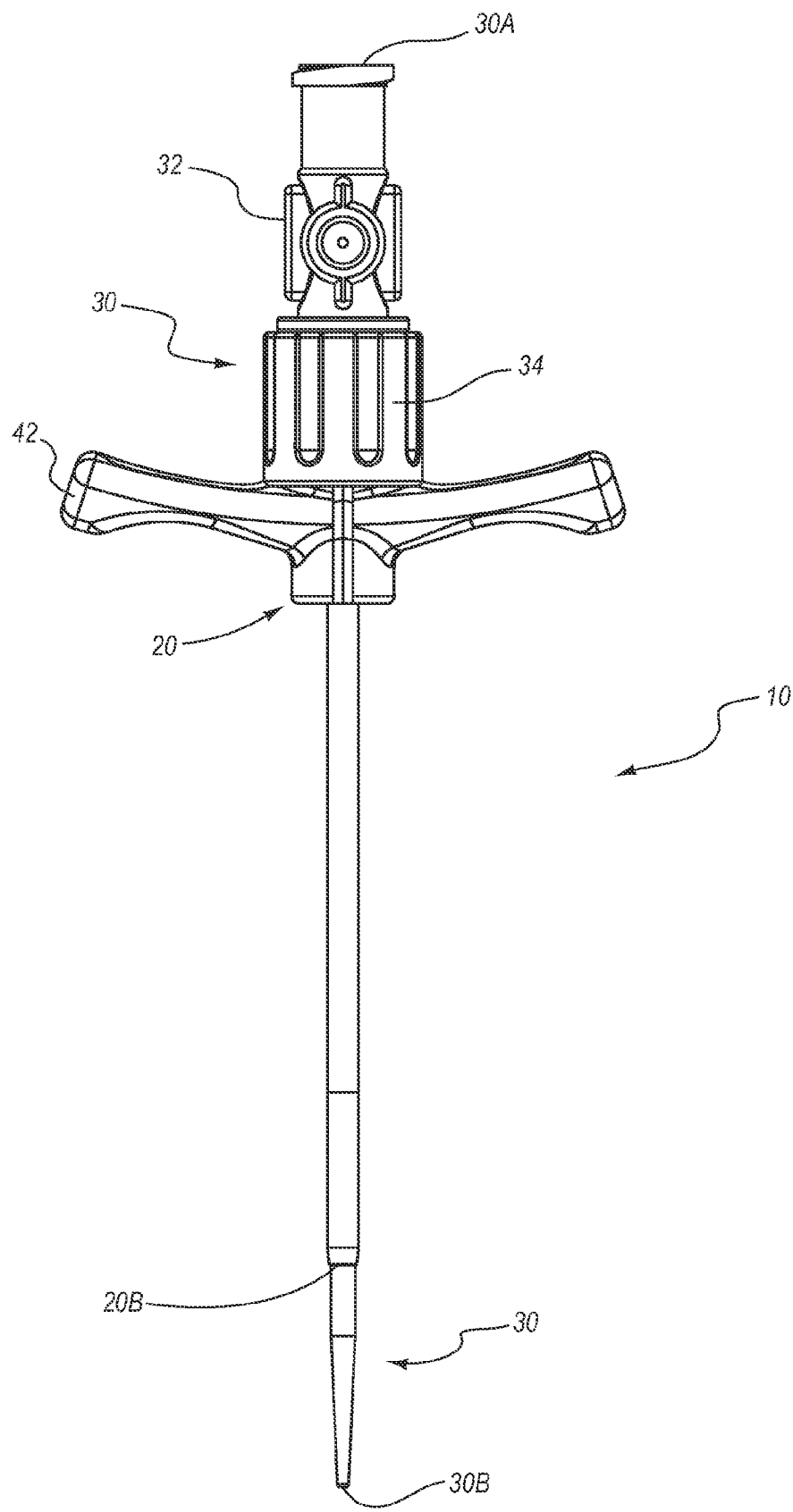
FIG. 1B is a side view of the introducer of FIG. 1A.

Reference is first made to FIGS. 1A-1B, which depict various details of an introducer, generally designated at 10, which is employed in accessing a vessel, such as a vein, or other portion of a patient's vasculature. In the present embodiment, the introducer 10 generally includes a sheath assembly 20 and a dilator 30. The dilator 30 defines an elongate shaft that is sized so as to be removably received within a hollow bore of the sheath assembly 20 such that a distal end 30B of the dilator extends a predetermined distance beyond an open distal end 20B of the sheath assembly 20, as shown in FIG. 1B. A hub 32 and locking nut 34 are included on a proximal end 30A of the dilator 30 for use in manipulating the dilator during introducer use. The locking nut 34 is threaded so as to threadingly engage a portion of a handle 42 disposed at a proximal end 20A of the sheath assembly 20. Other connective configurations between the handle and the dilator are also possible. A hollow sheath body 44 of the sheath assembly 20 extends distally from the handle 42 at the proximal end 20A to the distal end 20B thereof and defines the majority of the bore into which the dilator 30 is selectively received. A hole (FIG. 2B) is defined in the handle 42 and is in coaxial communication with the bore of the sheath body 44.

The dilator 30 defines a bore extending between its proximal end 30A and distal end 30B so as to enable the introducer 10 to be advanced over a guidewire or other suitable device during insertion into the vasculature, the guidewire having been pre-inserted through incisions in the skin and vein or other vessel into the vasculature. During such advancement, the introducer is assembled as shown in FIG. 1B. So assembled, a tapered region 60 of the dilator, to be discussed further below, extends from the dilator distal end 30B to at least the distal end 20B of the sheath assembly 20. As such, the tapered region 60 enables the dilator 30 to enlarge the incision previously defined in the vein or other vessel in preparation for the insertion of a PICC or medical device. Once the incision has been enlarged, the dilator 30 can be removed from the sheath assembly 20 and the PICC can be inserted through the vein incision and into the patient's vasculature via the sheath body 44.

Figure 3:
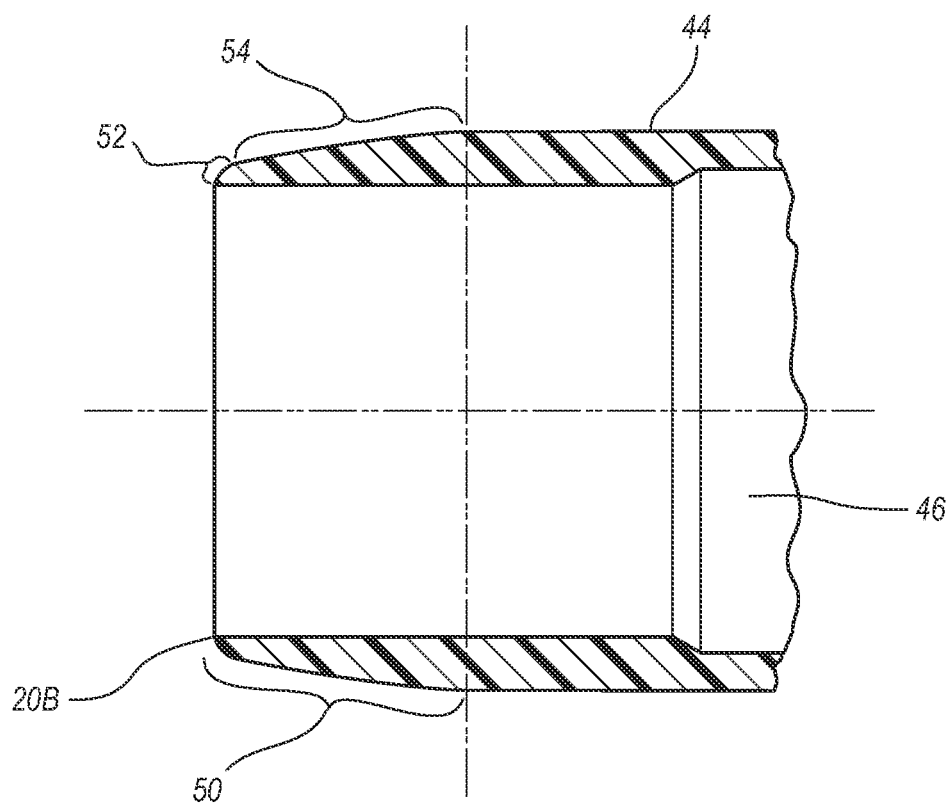
FIG. 3 is a cross sectional view of a shaped distal region of the sheath assembly of FIG. 2A, showing various aspects thereof, according to one embodiment.

Reference is now made to FIGS. 2A-3 in describing further details regarding the sheath assembly 20. As mentioned, the sheath assembly includes the sheath body 44, which defines a substantially cylindrical bore extending between the proximal end 20A and distal end 20B thereof. The handle 42 at the proximal end 20A of the sheath assembly 20 is attached to the sheath body 44 and is splittable such that the sheath assembly can be separated into two along a dividing plane 48 corresponding to the longitudinal length of the sheath body. This enables the sheath assembly 20 to be split apart during removal of the sheath from the vein. In the present embodiment the sheath body 44 is composed of polytetrafluoroethylene ("PTFE"), which provides relative ease of longitudinal splitting of the body. Note, however, that other materials can be alternatively employed to form the sheath including, for instance, fluorinated ethylene propylene ("FEP").

In accordance with one embodiment, a distal region of the sheath body 44 is shaped so as to ease entry of the introducer into the patient's vein or other vessel. As shown in FIG. 3, this is realized by including a shaped region 50 on an outer surface of the distal region of the sheath body 44. In particular, the shaped region 50 includes a first curved portion 52 cross sectionally defined by a first radius and a second curved portion 54 cross sectionally defined by a second radius. The first curved portion 52 extends proximally on the sheath body outer surface a predetermined distance from the sheath distal end 20B, while the second curved portion 54 extends proximally a predetermined distance from the proximal terminus of the first curved portion. Proximally of the second curved portion, the sheath body outer surface defines a substantially cylindrical shape. So configured, the first and second curved portions 52 and 54 define annular surfaces about the outer surface of the sheath body 44 proximate the distal end 20B of the sheath assembly 20.

As seen FIG. 3, the cross section of the first curved portion 52 is defined by a small radius and proximally extends a short distance relative to the radius and extension of the second curved portion 54. This enables the wall of the sheath body 44 to increase to a sufficient thickness within a relatively short distance proximal to the sheath distal end 20B while still providing a smooth transition region between the distal end and the more proximal portion of the sheath body outer surface. Similarly, the relatively longer extension and larger radius defining a cross section of the second curved portion 54 continues a transition in the increase of the outer diameter of the sheath body outer surface proximally from the distal end 20B. Thus, the shaped region 50 differs from a traditional sheath end taper, which taper results in substantial thinning of the sheath wall near the distal end thereof, undesirably contributing to fishmouthing or other undesired distal end deformation.

Configured as shown in FIG. 3, the distal end 20B of the sheath assembly 20 is provided a rounded profile by the first curved portion 52. Further, the distal region of the sheath assembly is more generally provided a bluntly rounded, or bullet-shaped, cross sectional profile by the configuration of the shaped region 50 as discussed above. As will be seen, introducer performance is improved as a result of this configuration. Of course, the relative longitudinal length and radius values of both curved portions can vary according to size, use, or other configuration of the introducer. Additionally, it is appreciated that the first and second curved portions can define other curved surfaces including oval or parabolic sections, for instance.

The value of the first and second radii that respectively define the first and second curved portions 52 and 54 can vary according to the size or other aspect of the introducer 10. Table 1 gives possible radius values for the cross sectional shapes of the first and second curved portions according to French size of the introducer, according to one possible implementation. Of course, these values are exemplary only and merely illustrative of the size variation possible with the shaped region of the introducer. It is further noted that the principles described herein apply to introducers of various configurations, including microintroducer, macrointroducers, valved introducers, etc.

TABLE 1

| Radius Values According to Introducer French Size | | |
|---|---|---|
| Introducer French Size (Fr.) | Radius of First Curved Portion (in.) | Radius of Second Curved Portion (in.) |
| 3.5 | .005 | .221 |
| 4.5 | .005 | .230 |
| 5 | .005 | .234 |
| 6 | .007 | .241 |
| 6.5 | .010 | .150 |
| 7 | .010 | .156 |
| 8 | .010 | .163 |
| 10 | .010 | .177 |
| 13 | .010 | .195 |
| 14 | .010 | .205 |
| 15 | .010 | .209 |
| 16.5 | .010 | .218 |

The longitudinal distance the shaped region 50 extends from the distal end 20B of the sheath assembly generally varies according to the size of the introducer, but in the case of a 5 Fr. introducer for instance, the shaped region extends a distance of approximately 0.05 inches proximally from the sheath assembly distal end 20B. Other shaped region extension distances are also possible.

Notwithstanding the above discussion, it is appreciated that the length, magnitudes and shape configurations of the sheath assembly distal portion can be varied from what is described herein while still residing within the scope of present invention. For instance, the shaped region can include more than two curved portions, if desired. Or, the curved portions can include straight bevels in addition or alternative to the curved surfaces. Thus, these and other possible modifications to the sheath assembly are contemplated as included within the principles of the present invention.

Figure 4:
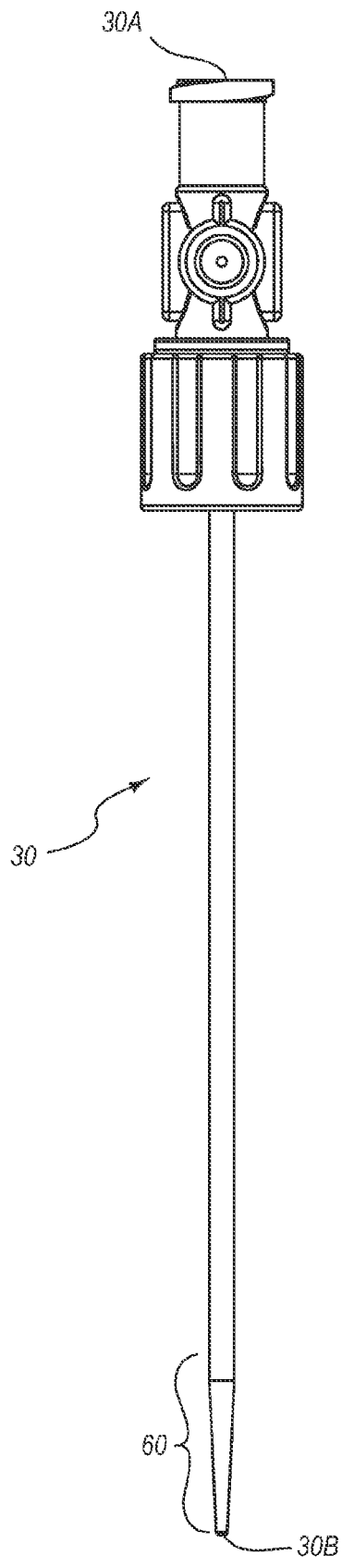
FIG. 4 is a partial cross sectional side view of a dilator of the introducer shown in FIG. 1A.
Figure 5:
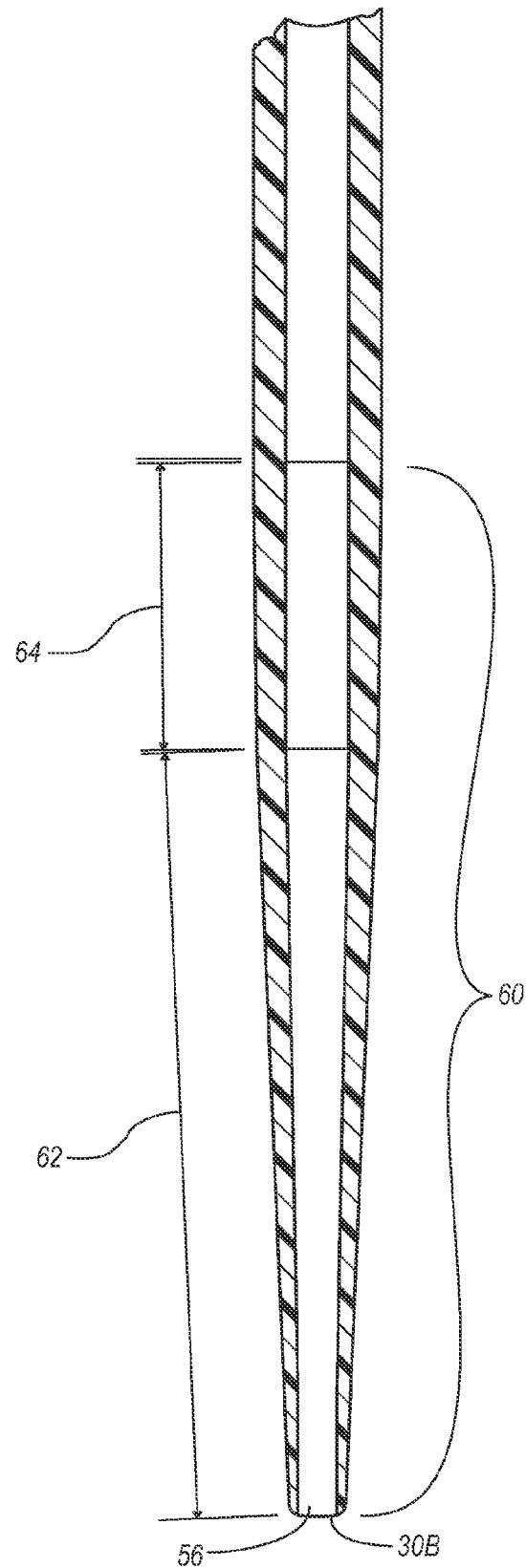
FIG. 5 is a cross sectional view of a distal region of the dilator showing various aspects thereof, according to one embodiment.

Reference is now made to FIGS. 4 and 5. As already discussed, the dilator 30 is received within the sheath assembly 20 such that the tapered region 60 of the dilator extends from the distal end 20B of the sheath assembly. The tapered region 60 enables the dilator 30 to enlarge the incision previously defined in the vein or other vessel in preparation for the insertion of a PICC or medical device into the patient's vasculature.

In greater detail, the dilator 30 includes an inner bore 56 extending from the dilator proximal end 30A and through the hub 32, locking nut 34, and dilator body to the dilator distal end 30B for receiving a guidewire therethrough. In the present embodiment, the tapered region 60 on the outer surface of the distal portion of the dilator 30 includes a first tapered portion 62 defining a first taper angle, and a proximally adjacent second tapered portion 64 defining a second taper angle. As shown in FIG. 5, the first tapered portion 62 extends from the dilator distal end 30B to a predetermined proximal endpoint, while the second tapered portion 64 extends from the proximal endpoint of the first tapered portion 62 to its respective proximal endpoint. As will be discussed, in one embodiment the proximal endpoint of the second tapered portion 64, as part of the tapered region 60, terminates longitudinally proximal to the point where the dilator 30 extends from the distal end 20B of the sheath assembly to provide an interference fit between the dilator and the sheath body 44. In other embodiments, the longitudinal extension of the tapered region 60 from the dilator distal end 30B can vary according to introducer size and configuration. For instance, the tapered region can extend proximally to the point where the dilator 30 extends from the distal end 20B of the sheath assembly 20, or can extend further proximally along the dilator body than what is described above.

The taper angles of the first tapered portion 62 and the second tapered portion 64 in one embodiment fall within a range of approximately five (5) to eight (8) degrees and one (1) to four (4) degrees, respectively. These ranges are merely exemplary, however, and it is appreciated that each tapered portion can define one of a variety of possible taper angles, according to need or desired configuration. Indeed, it is also appreciated that the tapered portion can include only one tapered portion, or more than two tapered portions.

Figure 6:
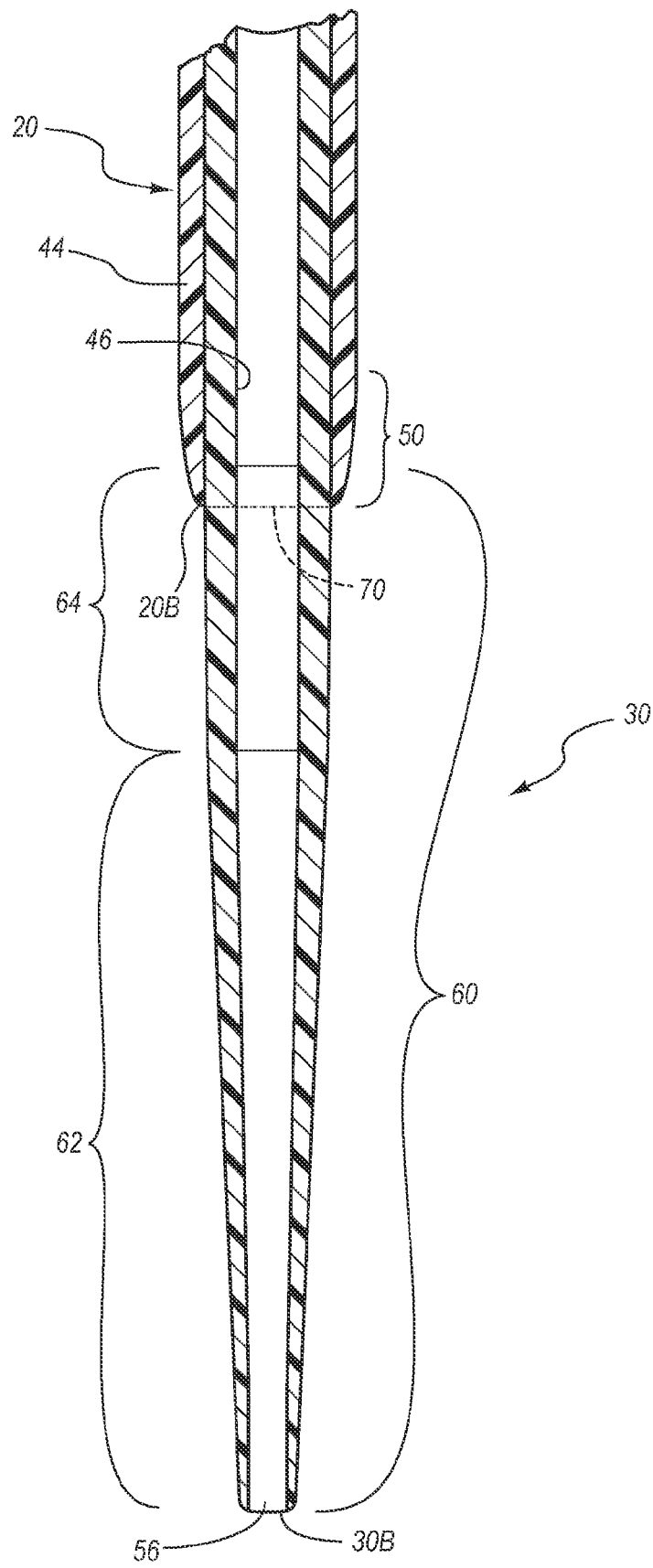
FIG. 6 is a cross sectional view of a distal region of the introducer of FIG. 1A, showing various aspects thereof, according to one embodiment.
Figure 7:
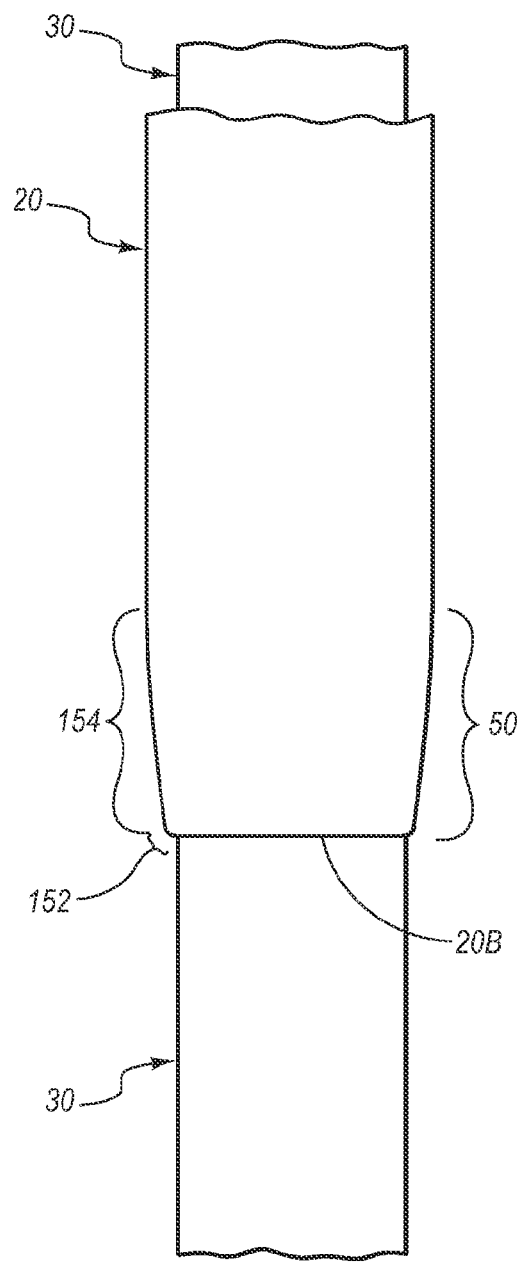
FIG. 7 is a side view of a portion of an introducer, showing aspects of a distal region of a sheath assembly according to another embodiment of the present invention.
Figure 8:
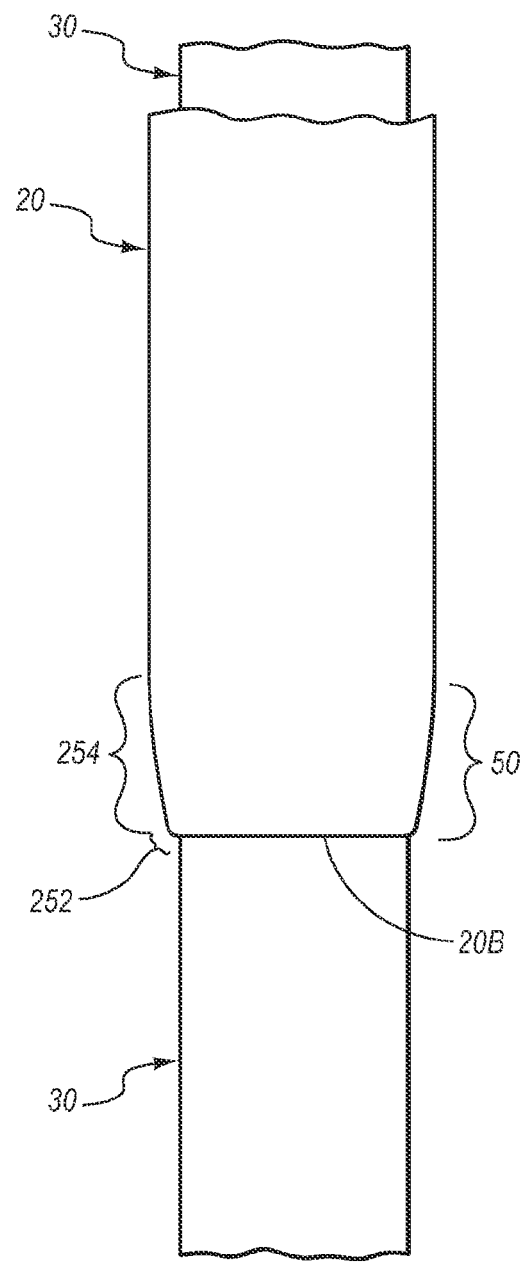
FIG. 8 is a side view of a portion of an introducer, showing aspects of a distal region of a sheath assembly according to yet another embodiment of the present invention.

Reference is now made to FIG. 6, which depicts the distal region of the introducer 10 in cross section. As shown, the dilator 30 exits distally from a sheath body central inner bore 46 at the distal end 20B of the sheath assembly 20, a point designated here as interface 70. The second tapered portion 64 of the outer surface of the dilator 30 extends proximally past the interface 70 and into the sheath body inner bore 46 when the dilator 30 and sheath assembly 20 are mated. So configured, an interference fit is achieved in the illustrated embodiment between the outer surface of the dilator 30 and the inner surface of the sheath assembly 20 at its distal end 20B at the interface 70.

In light of the above discussion, it can be seen that the introducer 10 as described herein is advantageously configured to reduce or preclude the incidence of peelback ("fishmouthing") or other undesired deformation of the sheath assembly distal end during insertion of the introducer into the patient vasculature. First, the shaped region 50 of the distal portion of the sheath body 44 includes the first and second curved portions 52 and 54. These curved portions prevent deformation or peeling away of the distal end 20B of the sheath assembly 20 from the dilator 30 should the sheath distal end encounter resistance or an obstacle during introducer insertion by providing a smoothly curved and transitioning outer surface while also ensuring sufficient sheath wall thickness at the distal end thereof. This in turn enables the sheath to proceed past the obstruction or resistance without damaging the sheath assembly or patient vasculature.

Second, and as already described in connection with FIG. 6, the tapered region 60 of the dilator 30 extends proximally through the sheath assembly distal end 20B and into the inner bore 46 of the sheath body 44. This provides an interference fit between the dilator 30 and the sheath body 44 at the interface 70, thus eliminating any gap between the two components and further reducing the likelihood of peelback or deformation of the distal end of the sheath body 44. In another embodiment it is appreciated that, alternatively, the inner diameter of the sheath body inner bore 46 could be reduced proximate the sheath assembly distal end 20B to provide a similar interference.

Figure 9A:
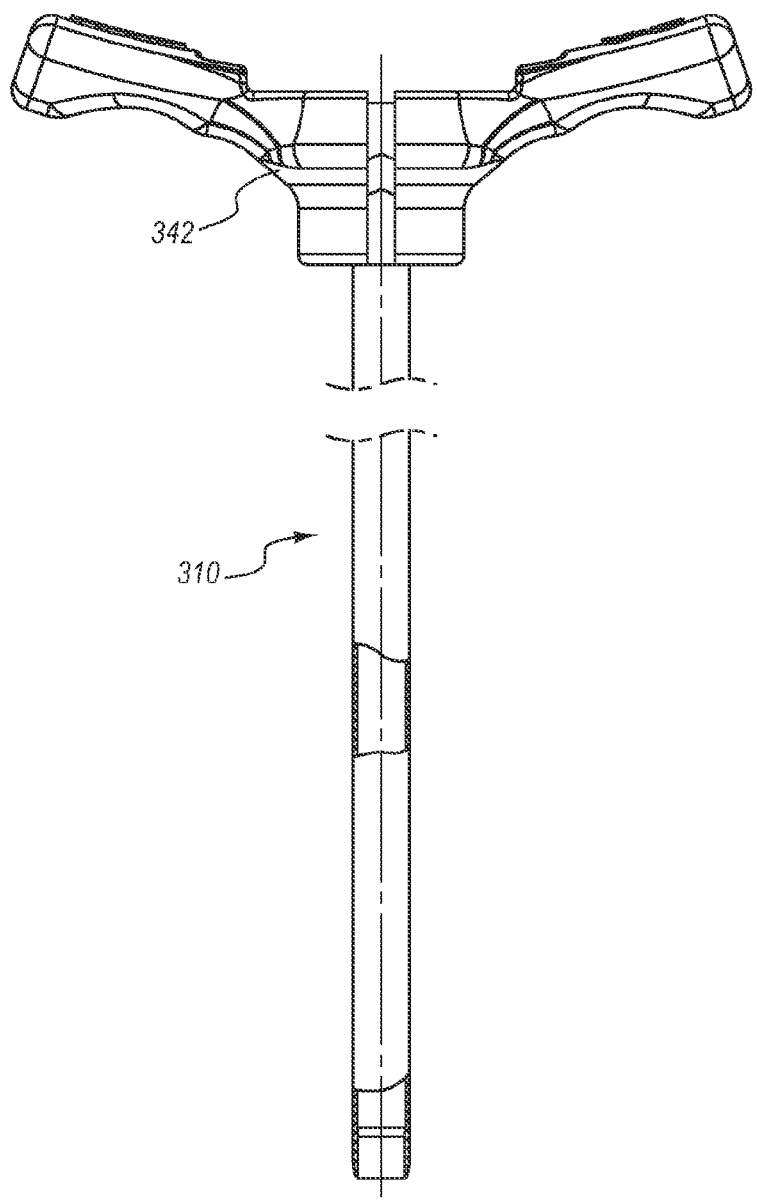
FIG. 9A is a partial cross sectional side view of a sheath assembly according to still another embodiment of the present invention.
Figure 9B:
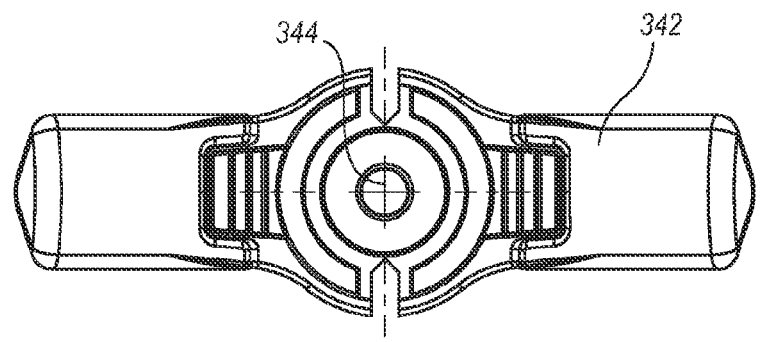
FIG. 9B is an end view of the sheath assembly of FIG. 9B.

It should be appreciated that the shaped region proximate the distal end of the sheath assembly can be configured in various ways to achieve the beneficial effects described immediately above. Examples of this can be found in FIGS. 7 and 8, which each depict a shaped region 50 at the distal end 20B of the sheath assembly 20. In particular, the shaped region 50 of FIG. 7 proximally extends a distance of approximately 0.075 in. from the sheath assembly distal end 20B and includes both a first curved portion 152 cross sectionally defined by a radius of approximately 0.005 in. and a second curved portion 154 cross sectionally defined by a radius of approximately 0.463 in. Similarly, the shaped region 50 of FIG. 8 proximally extends a distance of approximately 0.05 in. from the sheath assembly distal end 20B and includes both a first curved portion 252 cross sectionally defined by a radius of approximately 0.003 in. and a second curved portion 254 cross sectionally defined by a radius of approximately 0.234 in. In yet another example, FIGS. 9A and 9B depict a sheath assembly 310 including a handle 342 into which is incorporated a valve 344 for preventing the aspiration of fluids or infusion of air during introduction of the introducer into the patient's vasculature. The valved sheath assembly 310 can include a shaped region on its distal end and can receive a dilator having a tapered region similar to the previous embodiments discussed herein. These embodiments are therefore exemplary of a variety of possible configurations that may be utilized in connection with an introducer of the present invention.

Aspects of the present invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. An introducer for introducing a medical device into a vasculature of a patient, comprising:
   a sheath defining a proximal end, an open distal end, and a central bore extending therebetween, a distal region of the sheath including at least one curved outer surface portion proximally extending from the distal end thereof, a cross section of the at least one curved outer surface portion at least partially defined by a first radius; and
   a dilator that is removably received within the central bore of the sheath such that at least a portion of a distal tapered region of the dilator extends proximally into the central bore of the sheath when the dilator and sheath are mated wherein the sheath further includes a second curved outer surface portion cross sectionally defined by second radius, and wherein the at least one curved outer surface portion and the second curved outer surface portion provide a bullet-shape cross sectional profile to the distal end of the sheath.

2. The introducer as defined in claim 1, wherein the at least one curved outer surface portion provides an annular rounded surface to the distal end of the sheath.

3. The introducer as defined in claim 1, wherein a composition of the sheath includes polytetrafluorethylene.

4. The introducer as defined in claim 1, wherein the at least one curved outer surface portion extends approximately 0.05 inches proximally from the distal end of the sheath.

5. A sheath assembly for use with an introducer in introducing a medical device into a vasculature of a patient, comprising:
a sheath defining a proximal end, an open distal end, and a central bore extending therebetween, a distal region of an outer surface of the sheath including:
a first curved portion defined in cross section by a first radius and extending proximally from the sheath distal end to a first endpoint; and
a second curved portion defined in cross section by a second radius and extending proximally of the first endpoint to a second endpoint.

6. The sheath assembly as defined in claim 5, wherein the second curved portion is contiguous with the first curved portion.

7. The sheath assembly as defined in claim 5, wherein the central bore of the sheath is sized to receive a dilator therethrough, the dilator including a distal tapered region.

8. The sheath assembly as defined in claim 7, wherein the distal tapered region of the dilator includes a first tapered portion defined by a first taper angle and a second tapered portion defined by a second taper angle.

9. The sheath assembly as defined in claim 8, wherein a proximal termination of the second tapered portion is disposed proximally of the distal end of the sheath when the dilator is seated within the central bore of the sheath such that the second tapered portion extends into the central bore.

10. The sheath assembly as defined in claim 5, wherein an inner diameter of a wall defining the distal region of the sheath is substantially constant wherein the at least one curved outer surface portion and the second curved outer surface portion provide a bullet-shape cross sectional profile to the distal end of the sheath.

11. The sheath assembly as defined in claim 5, wherein an inner diameter of a wall defining the distal region of the sheath is smaller adjacent the distal end relative to a more proximal portion of the wall defining the distal region.

12. The sheath assembly as defined in claim 5, wherein the first and second curved portions are annularly defined on the outer surface of the sheath.

13. The sheath assembly as defined in claim 5, wherein the second radius of the second curved portion of the sheath is larger than the first radius of the first curved portion.

14. The sheath assembly as defined in claim 5, wherein the first radius of the first curved portion has a magnitude of from about 0.003 inch to about 0.010 inch.

15. The sheath assembly as defined in claim 5, wherein the second radius of the second curved portion has a magnitude of from about 0.15 inch to about 0.5 inch.

16. The sheath assembly as defined in claim 5, wherein the first and second curved portions are convexly shaped with respect to an exterior view of the sheath distal region.

17. An introducer for introducing a medical device into a vasculature of a patient, the introducer comprising:
a dilator including a distal tapered region; and
a sheath including an inner bore extending between a proximal and a distal end thereof for removably receiving the dilator therein such that at least a portion of the distal tapered region of the dilator distally extends from the distal end of the sheath, an outer surface of the sheath including:
a first curved portion cross sectionally defined by a first radius and extending proximally from the distal end of the sheath to a first end point; and
a second curved portion cross sectionally defined by a second radius and extending proximally from the first end point to a second end point.

18. The introducer as defined in claim 17, wherein the first and second curved portions assist in preventing deformation of the distal end of the sheath during introduction of the introducer into the patient vasculature.

19. The introducer as defined in claim 18, wherein the introducer is used to insert a catheter into the patient vasculature.

20. The introducer as defined in claim 19, wherein the distal tapered region of the dilator extends into the bore of the sheath so as to provide an interference fit between the dilator and the distal end of the sheath.

21. The introducer as defined in claim 20, wherein the distal tapered region includes a first tapered portion defined by a first taper angle and extending proximally from a distal end of the dilator and a second tapered portion defined by a second taper angle and extending proximally from a proximal end point of the first tapered portion.

22. The introducer as defined in claim 21, wherein the first taper angle has a magnitude of from about five (5) to eight (8) degrees, and wherein the second taper angle has a magnitude of from about one (1) to four (4) degrees.

23. The introducer as defined in claim 22, wherein the first and second curved portions together extend proximally at least 0.05 inch from the distal end of the sheath.

24. The introducer as defined in claim 23, wherein the sheath is splittable and wherein the proximal end of the sheath includes a splittable handle, the handle including a threaded connector for threadably engaging a locking nut disposed on a proximal portion of the dilator.

25. The introducer as defined in claim 24, wherein the dilator defines a longitudinal bore for receiving a guidewire therethrough.

* * * * *